United States Patent [19]
Bischof et al.

[11] Patent Number: 5,633,396
[45] Date of Patent: May 27, 1997

[54] PROCESS FOR PREPARING TRIISOCYANATES

[75] Inventors: Eric Bischof, Leichlingen; Jürgen Dahmer, Köln; Andreas Flink, Dormagen; Wolfgang Krohn, Köln; Attila Molnar, Odenthal, all of Germany

[73] Assignee: Bayer Aktiengesellschaft, Leverkusen, Germany

[21] Appl. No.: 666,725

[22] Filed: Jun. 17, 1996

[30]  Foreign Application Priority Data

Jun. 23, 1995 [DE] Germany ................. 195 23 385.9

[51] Int. Cl.⁶ ................................................. C07C 263/10
[52] U.S. Cl. ............................................................ 560/347
[58] Field of Search .................................... 560/347

[56]  References Cited

U.S. PATENT DOCUMENTS

| | | | |
|---|---|---|---|
| 4,314,048 | 2/1982 | Doi et al. | 528/44 |
| 4,847,408 | 7/1989 | Frosch et al. | 560/347 |
| 5,449,818 | 9/1995 | Biskup et al. | 560/347 |

FOREIGN PATENT DOCUMENTS

| | | |
|---|---|---|
| 2146522 | 10/1995 | Canada . |
| 60-233043 | 11/1985 | Japan . |
| 60-233044 | 11/1985 | Japan . |

*Primary Examiner*—Samuel Barts
*Attorney, Agent, or Firm*—Joseph C. Gil; Lyndanne M. Whalen

[57] ABSTRACT

Triisocyanates are produced by gas phase phosgenation of the corresponding (cyclo)aliphatic triamines having three primary amine groups.

6 Claims, No Drawings

PROCESS FOR PREPARING TRIISOCYANATES

BACKGROUND OF THE INVENTION

The present invention relates to a gas phase process for preparing cycloaliphatic and aliphatic (hereinafter "(cyclo)aliphatic") triisocyanates.

Although the preparation of organic isocyanates by reacting amines with phosgene in the gas phase has been known for some time (see, e.g., Siefken, Justus Liebigs Ann. Chem. 562, 108 (1949).), such preparation has only been recommended for monoisocyanates (e.g., Ullmanns Encyklopädie der technischen Chemie, 4th ed. Vol. 13, page 353), (cyclo)aliphatic diisocyanates (EP-A-0,289,840 and German Patent Application P 44 12 327.2), or for the preparation of aromatic diisocyanates (DE-OS 4,217,019).

Although (cyclo)aliphatic triisocyanates are mentioned in the literature, these triisocyanates are not available on an industrial scale. In fact, these triisocyanates are not obtainable in commercial yields by the classical process of phosgenating the corresponding triamines in the liquid phase. This is due to the low yields of crude product and the mechanical problems encountered during preparation by this process.

Traditional phosgenation of 1,8-diamino-4-aminomethyloctane in the liquid phase yields 74% of the desired triisocyanate, with respect to the amine used (DE-C-3,109,276). The disadvantage of the process disclosed in DE-C-3,109,276 are both the low yield and mechanical problems. These mechanical problems indicate either that reliable stirring of the reaction mixture is very difficult or that extremely high dilution with solvents is required during phosgenation. These disadvantages may be partially reduced, according to the disclosures in Jp-A-60,233,043 and JP-A-60,233,044, by mixed phosgenation of the triamines with aromatic or aliphatic diamines. The disadvantage of each of these processes, however, is the necessity for separation by distillation of the two polyisocyanates formed and the inevitable production of the particular diisocyanate.

SUMMARY OF THE INVENTION

It is an object of the present invention to provide a process for producing (cyclo)aliphatic triisocyanates in substantially higher yields.

It is also an object of the present invention to provide a process for producing (cyclo)aliphatic triisocyanates in which the mechanical problems of the known phosgenation processes are avoided without the need to use large amounts of solvent.

These and other objects which will be apparent to those skilled in the art are accomplished by phosgenating the corresponding triamine in the vapor phase at a temperature of from 200° to 600° C. in a cylindrical reaction chamber with no moving parts at a rate of flow of at least 3 m/s.

DETAILED DESCRIPTION OF THE INVENTION

The present invention relates to a process for the production of (cyclo)aliphatic triisocyanates. Phosgenation of triamines and subsequent working-up of the reaction mixture are carried out in a process analogous to that described in EP-A-0,289,840. The substantial improvement in yield achieved by the process of the present invention could not have been expected because the poor yields of triisocyanate obtained by the known prior art processes are attributed to the side reactions which occur during the phosgenation reaction. These side reactions are attributable to the high functionality of the amine starting material. It could not have been foreseen that these side reactions would not occur to any significant extent during gas phase phosgenation.

The present invention produces triisocyanates represented by the general formula

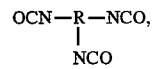

in which
R represents a (cyclo)aliphatic hydrocarbon group having from 1 to 22 carbon atoms, by phosgenation of the corresponding triamines represented by the general formula

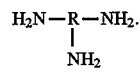

This process is carried out using triamines in the vapor form, optionally diluted with an inert gas or the vapor of an inert solvent. The triamines and diluent are heated to a temperature of from 200° to 600° C. and the phosgene is also heated to from 200° to 600° C. The heated amine and phosgene are continuously reacted together in a cyclindrical reaction chamber without any moving parts that is heated to 200° to 600° C. while maintaining a rate of flow in the reaction chamber of at least 3 m/s. The gas mixture continuously leaving the reaction chamber is cooled with the assistance of an inert, liquid solvent which is maintained at a temperature above the decomposition temperature of the carbamic acid chloride corresponding to the triamine. A solution of the triisocyanate in this solvent is recovered. The triisocyanate which is dissolved in the inert solvent is subjected to working-up by distillation.

The triamines to be used as starting materials in the process of the present invention include those represented by the general formula:

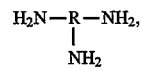

in which
R is defined as above.
Preferred triamines are those in which
R represents a saturated (cyclo)aliphatic hydrocarbon group having from 4 to 22, more preferably from 6 to 15 and most preferably from 7 to 11 carbon atoms in which at least 2 carbon atoms are located between each 2 amino groups.

The term "(cyclo)aliphatic" as used herein is intended to include both open-chain aliphatic hydrocarbon groups and also hydrocarbons having cycloaliphatic structural units present in which the amino groups may be aliphatically and/or cycloaliphatically bonded.

Examples of triamines useful in the practice of the present invention include: 1,8-diamino-4-(aminomethyl)-octane; 1,6, 11-undecanetriamine; 1,7-diamino-4-(3-aminopropyl)-heptane; 1,6-diamino-3-(aminomethyl)-hexane; and 1,3,5-tris-(aminomethyl)-cyclo-hexane. Basically, however, the starting material used may be any (cyclo)aliphatic triamine with from 1 to 22 carbon atoms, provided that it is stable under the thermal conditions used in the process of the present invention and can be converted into the vapor form.

Suitable starting materials also include any triaminocyclohexanes; tris-(aminomethyl)-cyclohexanes; triaminomethyl-cyclohexanes; and comparable triamines.

The triamine starting material is evaporated before phosgenation in accordance with the process of the present invention and is continuously heated to a temperature within the temperature range of from 200° to 600° C., preferably from 300° to 500° C. The heated triamine vapor can be used in the process of the present invention as such or in a dilute form with inert gas or with the vapor of an inert solvent. Mixing of the triamine vapor with the inert gas can be performed, for example, by evaporating the triamine into a stream of an inert gas or the vapor of an inert solvent. The inert gas is preferably nitrogen. Suitable inert solvents whose vapors can also be used to dilute the triamine include: chlorobenzene, o-dichloro-benzene, xylene, chloronaphthalene, decahydronaphthalene and mixtures thereof.

The amount of inert gas or solvent vapor optionally used as diluent is not critical. The inert gas or solvent vapor may be used to lower the evaporation temperature of the amine.

The phosgene used for phosgenation is used in excess, with respect to the triamine. In general, an amount of phosgene which corresponds to 150 to 300% of the theoretical amount is sufficient.

Before being used in the process of the present invention, the stream of phosgene is heated to a temperature in the range of from 200° to 600° C., preferably from 300° to 500° C.

In the process of the present invention, the pre-heated streams of triamine or triamine/inert gas mixture and of phosgene are continuously passed into a cylindrical reaction chamber where they are mixed with each other.

Suitable cylindrical reaction chambers include tubular reactors without baffles and without any moving parts inside the reactor. Tubular reactors are generally made up of steel, glass, alloyed or enamelled steel and have a tenth which is sufficient to enable complete reaction of the triamine with phosgene under the conditions of the process. The gas streams are generally introduced into the tubular reactor at one end. This introduction may be performed through nozzles fitted at one end of the tubular reactor or by a combination of a nozzle and an annular gap between the nozzle and mixing tube. The mixing tube is also maintained at a temperature in the range of from 200° to 600° C., preferably from 300° to 500° C. This temperature is optionally held constant by heating the reaction tube.

When conducting the process of the present invention, the pressure in the supply piping to the reaction chamber is generally from about 200 to about 3000 mbar and at the outlet from the reaction chamber is from about 150 to about 2000 mbar. Care should be taken to provide a flow-rate inside the reaction chamber of at least 3, preferably at least 6 and most preferably from about 10 to 120 m/s. This may be accomplished by maintaining an appropriate pressure difference. Turbulent flow characteristics generally prevail inside the reaction chamber.

The triisocyanate formed by phosgenation in accordance with the present invention is removed from the gaseous mixture continuously leaving the reaction chamber. This may be performed, for example, using an inert solvent at a temperature which is above the decomposition temperature of the carbamic acid chloride corresponding to the triisocyanate but below the condensation temperature of the triisocyanate and preferably also of the solvent optionally used as diluent in the vapor form. The triisocyanate and auxiliary solvent will condense or dissolve in the solvent, while excess phosgene, hydrogen chloride and inert gas optionally used as diluent will pass through the condensation stage or the solvent in the gasous form. For selective recovery of the triisocyanate from the gaseous mixture leaving the reaction chamber, solvents of the type mentioned above (particularly technical grade dichlorobenzene) held at a temperature of from 120° to 200° C., preferably from 120° to 170° C., are highly suitable. Examples of possible methods for selectively condensing the triisocyanate formed from the gas mixture leaving the reactor using this type of solvent are passing the gas mixture through the solvent or spraying the solvent (mist) into the gas stream.

Excess phosgene may be removed from the gas mixture passing through the condensation stage for recovering the triisocyanate by any of the known methods. This may be accomplished by means of a cold trap, absorption in an inert solvent held at a temperature of from −10° C. to 8° C. (e.g. chlorobenzene or dichlorobenzene) or by adsorption and hydrolysis on activated carbon. The hydrogen chloride gas passing through the phosgene recovery stage may be recycled in known manner in order to recover the chlorine requested to synthesize phosgene.

The triisocyanates produced by this process may be purified by distilling the solution of triisocyanate in the solvent used for triisocanate condensation.

Having thus described our invention, the following Example is given as being illustrative thereof. All percentage data given in this Example are percentages by weight.

EXAMPLE

The apparatus used in this process was a mixing tube having a diameter of 2.5 mm and a length of 17.5 mm (heated to 510° C.) with a downstream triisocyanate condensation stage and, following this, a phosgene adsorption tower filled with activated carbon. Through a nozzle which projected into the mixing tube, was continuously flowed 8 mol/hour of phosgene which had been heated to a temperature of 460° C. in an upstream heat exchanger, at a pressure of 950 mbar. Through an annular gap between the nozzle and the mixing tube, a mixture of 0.4 mol/hour of 4-aminomethyl-1,8-octanediamine and 0.1 mol/hour of nitrogen (as diluent) heated to 410° C. were introduced into the mixing tube at the same time. The rate of flow in the reaction chamber was 100 m/s. By applying a vacuum at the end of the triisocyanate condensation stage, a pressure of about 350 mbar was maintained in the mixing tube. In the condensation stage the hot gaseous reaction mixture leaving the reaction chamber was passed through dichlorobenzene which was held at a temperature of from 150° to 160° C. Selective condensation of the triisocyanate formed was achieved in this way. The mixture passing through the washing stage, consisting essentially of nitrogen, hydrogen chloride and excess phosgene, the adsorption tower was subsequently introduced where the phosgene was then removed. The triisocyanate was obtained in pure form from the wash solution by means of distillation. The triisocyanate was obtained in pure form from the wash solution by means of distillation. The yield of pure triisocyanate was 92% of theoretical. The same triisocyanate was obtained in Example 2 of DE-C-3,109,276 in a yield of only 74% of theoretical.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for producing a triisocyanate represented by the general formula $$OCN-\underset{\underset{NCO}{|}}{R}-NCO,$$

in which

R represents a (cyclo)aliphatic hydrocarbon group having from 1 to 22 carbon atoms, comprising a) phosgenating (1) a triamine represented by the general formula $$H_2N-\underset{\underset{NH_2}{|}}{R}-NH_2.$$

which is present in vapor form and has been heated to a temperature of from 200° to 600° C.

by continuously reacting that triamine with (2) phosgene heated to from 200° to 600° C.

in a cylindrical reaction chamber heated to 200° to 600° C., without any moving parts, while maintaining a rate of flow in the reaction chamber of at least 3 m/s, b) cooling the gas mixture continuously leaving the reaction chamber with an inert, liquid solvent which is held at a temperature above the decomposition temperature of carbamic acid chloride corresponding to the triamine to recover a solution of the triisocyanate in the solvent and c) recovering the triisocyanate which is dissolved in the inert solvent.

2. The process of claim 1 in which the triamine is selected from 1,8-diamino-4-(aminomethyl)-octane, 1,6,11-undecanetriamine, 1,7-diamino-4-(3-aminopropyl)-heptane, 1,6-diamino-3-(aminomethyl)-hexane and 1,3,5-tris-(aminomethyl)-cyclohexane.

3. The process of claim 1 in which the reaction chamber is maintained at a temperature of from about 300° to 500° C.

4. The process of claim 1 in which the triamine is diluted with an inert gas or the vapor of an inert solvent.

5. The process of claim 4 in which nitrogen is used to dilute the triamine vapor.

6. The process of claim 1 in which the triisocyanate is recovered in c) by distillation.

* * * * *